Figure 1:
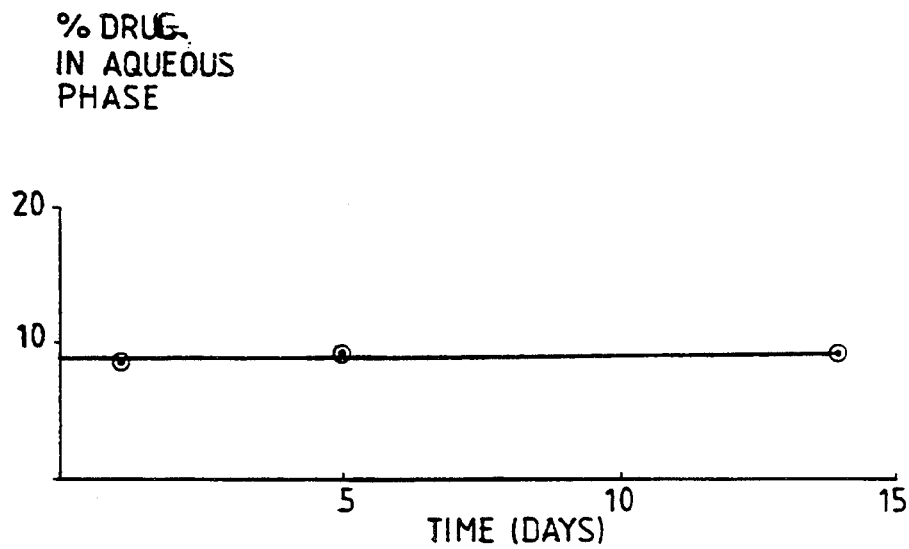

United States Patent [19]

Boyes et al.

[11] Patent Number: 5,384,133
[45] Date of Patent: Jan. 24, 1995

[54] PHARMACEUTICAL FORMULATIONS COMPRISING MICROCAPSULES

[75] Inventors: Robert N. Boyes, St. Albans, England; Thomas R. Tice, Birmingham, Ala.; Richard M. Gilley, Birmingham, Ala.; Kenneth L. Pledger, Huntsville, Ala.

[73] Assignee: Innovata Biomed Limited, Edinburgh, United Kingdom

[21] Appl. No.: 84,747

[22] Filed: Jun. 29, 1993

Related U.S. Application Data

[63] Continuation of Ser. No. 860,854, Mar. 27, 1992, abandoned, which is a continuation of Ser. No. 317,452, filed as PCT/6B87/00566, Aug. 11, 1987, abandoned.

[30] Foreign Application Priority Data

Aug. 11, 1986 [GB] United Kingdom ............... 8619519
Jan. 5, 1987 [GB] United Kingdom ............... 8700063

[51] Int. Cl.$^6$ .......................... A61K 9/12; A61K 9/14; A61K 9/40
[52] U.S. Cl. ........................ 424/501; 424/45; 424/489; 424/490; 424/491; 424/497; 514/826; 514/951; 514/927
[58] Field of Search ............... 424/45, 489, 490, 491, 424/497, 501, 43, 45, 450; 514/826, 951, 927, 272.3

[56] References Cited

U.S. PATENT DOCUMENTS

| | | | |
|---|---|---|---|
| 4,411,933 | 10/1983 | Samejima | 424/495 |
| 4,479,911 | 10/1984 | Fong | 264/46 |
| 4,569,844 | 2/1986 | Jones | 424/492 |
| 4,742,066 | 5/1988 | Deckner et al. | 514/917 |
| 4,781,871 | 11/1988 | West, III et al. | 424/450 |
| 4,837,028 | 6/1989 | Allen | 424/450 |
| 4,857,406 | 8/1989 | Schwab | 424/455 |
| 4,861,627 | 8/1989 | Mathiowitz | 427/213.31 |
| 4,895,719 | 1/1990 | Radhakrishman et al. | 424/45 |
| 4,952,402 | 8/1990 | Sparks | 424/419 |

FOREIGN PATENT DOCUMENTS

| | | |
|---|---|---|
| 165209B | 10/1992 | Denmark . |
| 0038979 | 11/1981 | European Pat. Off. . |
| 0121712 | 10/1984 | European Pat. Off. . |
| 147883 | 3/1983 | Norway . |
| 1540461 | 2/1979 | United Kingdom . |
| 8601714 | 3/1986 | WIPO . |
| 8701587 | 3/1987 | WIPO . |

OTHER PUBLICATIONS

Remington's Pharm. Sci. p. 1306, 1985.
Illum and Davis: "Polymers in Controlled Drug Delivery" 1987 pp. 6 to 11.
Duncan and Seymour: "Controlled Release Technologies" pp. 21 and 23.

*Primary Examiner*—Gollamudi S. Kishore
*Attorney, Agent, or Firm*—Harness, Dickey & Pierce

[57] ABSTRACT

Pharmaceutical formulations comprise (i) microcapsules which consist essentially of a biocompatible polymeric wall material encapsulating a drug, and (ii) a lipid soluble surfactant which is mixed with the microcapsules or is incorporated within or coats the wall material of the microcapsules. Such formulations may be presented as an aerosol or dry powder for inhalation. Microcapsules with surfactant incorporated in the wall material may be suspended in a pharmaceutically acceptable water-immiscible oil and the resulting suspension emulsified in an aqueous medium to obtain a formulation for oral administration.

25 Claims, 1 Drawing Sheet

PHARMACEUTICAL FORMULATIONS COMPRISING MICROCAPSULES

This is a continuation of U.S. patent application Ser. No. 07/860,854, filed Mar. 27, 1992, now abandoned which is a continuation of U.S. patent application Ser. No. 317,452, filed Apr. 3, 1989, now abandoned.

This invention relates to controlling the release of drugs from pharmaceutical formulations.

Currently available treatments for asthma and bronchitis, although generally effective, are limited by the necessity for frequent drug administration and/or the possibility of unpleasant or debilitating side effects. It has long been established that direct application of bronchodilating drugs to the lungs by inhalation provides rapid relief for asthmatic and bronchitic symptoms. However, the very rapid systemic absorption of drugs when administered by this route results in a relatively short duration of the desired clinical effect. Consequently this route of administration has not been as acceptable for the prophylatic administration of bronchodilating drugs in an attempt to prevent acute asthmatic attacks. Certain oral dosage forms are available for this latter purpose. However, they are not administered directly to the site of action. The dosages required are therefore very much higher and the incidence of unpleasant side effects is much greater.

The respiratory tract may also be used as a means of drug administration in circumstances where other routes are inappropriate or inconvenient. Certainly anaesthetic agents are administered by this route for their systemic activity, and there is evidence in the literature that peptides such as insulin can be absorbed systematically from the lungs.

The process of microencapsulation of drugs in various polymeric materials is a well known means of producing controlled release drug delivery systems. Factors controlling the release of drugs from these microcapsules have been well described in the literature. In summary the critical factors are:

1. the method of encapsulation and therefore the physical nature of the microcapsule;
2. the specific polymeric material chosen to form the walls of the microcapsule;
3. the physical state of the polymeric material in the microcapsule, i.e. the degree of crystallinity; and
4. the solubility and diffusion characteristics of the salt form of the drug chosen.

Children and the elderly have difficulty in swallowing conventional tablets and capsules. Unfortunately there have been many technical difficulties in producing controlled release drug delivery systems which could be administered in syrup or liquid form. The greatest technical difficulties are, on the one hand, of keeping the active ingredient largely out of aqueous solution during storage, while at the same time allowing this active ingredient to dissolve slowly once the product has been administered to a patient.

We have now produced microencapsulated drug particles typically in sizes ranging in excess of 1 um. The drugs employed have been incorporated in various polymeric wall forming materials. It was found that when these microcapsules were exposed to lipid-soluble surfactant or when such a surfactant was incorporated in the wall material of the microcapsule, the release of drug from the microcapsules was retarded. The rate of release of the drug could be controlled with respect to time.

Accordingly, the present invention provides pharmaceutical formulations suitable for inhalation, comprising:

(i) microcapsules having an average diameter of from 0.1 to 10 um which consist essentially of a biocompatible biodegradable polymeric wall material encapsulating a drug, and
(ii) a lipid-soluble surfactant which is mixed with the microcapsules or is incorporated within or coats the wall material of the microcapsules.

The invention further provides pharmaceutical compositions suitable for ingestion, comprising:

(i') microcapsules having an average diameter of from 0.1 to 20 um, which consist essentially of a biocompatible polymer wall material encapsulating a drug, and (ii) a lipid-soluble surfactant, which is mixed with the microcapsules or-is incorporated within or coats the wall material of the microcapsules.

Such formulations can be simple mixtures of microcapsules encapsulating a drug and surfactant. Alternatively or additionally, microcapsules encapsulating drug may have been exposed to surfactant so that the surfactant forms a coating on the wall material of the microcapsules. Microcapsules having surfactant incorporated in their walls may also be prepared by dissolving the polymeric material for the walls in a solvent, dispersing surfactant and drug in the polymer solution, evaporating off the solvent and obtaining the particles thus formed with the desired average diameter. A pharmaceutically acceptable carrier or diluent may be provided in the formulation.

The formulation may be presented in a form suitable for inhalation. For this purpose, it may take the form of an aerosol in which the microcapsules are suspended in the propellant for the aerosol or it may be in dry powder form. Use of the present system for local application of drugs to the lungs extends beyond bronchodilating agents. Other drugs important in the treatment of asthma may be administered in this way including corticosteroids, disodium cromoglycate antihistamines and leukotriene antagonists. Furthermore, slow release of antibiotic and antiviral materials, chemotherapeutic agents for cancer treatment in the lung may be achieved.

Alternatively, an orally administrable preparation may be formulated. A preferred such oral formulation is prepared by suspending the microcapsules incorporating the surfactant in their walls in a pharmaceutically acceptable water-immiscible oil and emulsifying the oil suspension of microcapsules in an aqueous medium.

By mixing the lipid-soluble surfactant with the microcapsules or incorporating the surfactant in the walls of the microcapsules, the release of drug from the microcapsules can be controlled. In its turn, this controls the degree and duration of the pharmacological effect obtained. As far as the preferred liquid oral dosage form is concerned, a drug release delivery system can be produced with is stable in the aqueous form but which releases drug in vivo at rates similar to that produced by various conventional long acting formulations. Further, the system is easier to administer to children and older patients. Protection of drugs by way of microencapsulation in the system can improve their stability in aqueous media. The flavour and palatability of liquid formulations may be improved.

The drug encapsulated in the microcapsules may be any agent which exhibits a pharmacological effect. The drug may be selected from antibiotics such as ampicillin or penicillin V, cardiovascular drugs such as betablockers, calcium antagonists or nitrates such as isosorbide dinitrate or isosorbide mononitrate, a drug for cough and cold preparations such as dextromethorphan or diphenhydramine, peptide drugs such as insulin or human growth hormone, other naturally occurring agents and derivatives such as prostaglandins, anti-vital agents and anti-convulsants such as phenytoin and sodium valproate.

Preferably, the drug is a bronchodilating agent. Suitable bronchodilator compounds include beta-receptor agonists and, more particularly, beta-adrenergic agonist agents such as salbutamol (2-tert.butylamino-1-(4-hydroxy-3-hydroxymethyl phenyl)ethanol, normally presented as its sulphate) and terbutaline (2-tert.butylamino-1-(3,5-dihydroxyphenyl)ethanol, normally presented as its sulphate). Other bronchodilating agents which may be employed are xanthines such as theophylline, anti-cholinergic agents such as ipatropium bromide and the like, calcium antagonists such as nifedipine and biological agents such as leukotrienes and derivatives thereof.

The amount of drug incorporated in the microparticles usually ranges from less than 1% to as high as 95% by weight, preferably from 1 to 80% by weight. Two or more drugs may be encapsulated in the microcapsules. In such an event, the drugs must be inert with respect to each other.

The polymeric wall material of the microcapsules must be biocompatible. A biocompatible polymeric material is a polymeric material which is not toxic to the human body, is not carcinogenic and should not induce inflammation in body tissues. Preferably, the wall material is biodegradable in the sense that it should degrade by bodily processes to products readily disposable by the body and should not accumulate in the body. For microcapsules for inhalation, therefore, the wall material should be biodegradable. Suitable examples of polymeric materials include poly(glycolic acid), poly-d,1-lactic acid copolymers thereof, copolyoxalates, polycaprolactone, poly(lactic acid-caprolactone), and the like. For oral preparations, cellulose derivatives such as ethyl cellulose may be employed.

The molecular weight of the polymeric material for the walls of the microcapsules should be high enough so that it forms satisfactory polymer coatings. Usually a satisfactory molecular weight is greater than 10,000 daltons. The molecular weight of a polymer is also important from the point of view that molecular weight influences the biodegradation rate of the polymer. By an appropriate selection of polymeric materials a formulation can be made such that the resulting microcapsules remain intact until all of the drug is released and then degrade.

The microcapsules may be prepared in any suitable fashion. They may be prepared by spray-drying. In this technique, the polymeric material for the walls of the microcapsules is dissolved in a solvent such as methylene chloride. An appropriate amount of surfactant, if desired, and drug, depending on the desired core load of the microcapsules, is dispersed in the polymer solution. This dispersion is then spray-dried. An inert gas such as nitrogen is typically forced through the nozzle of the spray-dryer with the dispersion to cause an aerosol of microcapsules to be formed initially. The microcapsules are then collected.

Alternatively, the microcapsules may be prepared by:

(a) dissolving or dispersing a drug in a solvent, typically methylene chloride, and dissolving a biocompatible and biodegradable wall forming material in the solvent;

(b) dispersing the solvent containing the drug and wall forming material in a continuous phase processing medium such as a 1 to 10% by weight polyvinyl alcohol in water mixture;

(c) evaporating a portion of the solvent from the dispersion of step (b) , thereby forming microcapsules containing the drug in suspension; and (d) extracting the remainder of the solvent from the microcapsules.

The microparticle product is usually made up of particles of a spherical shape although sometimes the microcapsules may be irregularly shaped. Microcapsules for inhalation have an average diameter of 0.1 to 10 um, preferably 1 to 5 um. Microcapsules for ingestion have an average diameter of from 0.1 to 20 um, preferably from 1 to 20 um.

The microcapsules incorporate a lipid-soluble surfactant as a drug release controlling agent. The surfactant is typically in liquid form. It is preferably a sorbitan fatty acid ester such as sorbitan trioleate, sorbitan monolaurate, sorbitan monooleate, sorbitan monopalmitate and sorbitan monostearate. Alternatively, the surfactant may be a polyoxamer or a surface active fatty acid such as oleic acid.

Where the formulation is a simple mixture of microcapsules and surfactant, the surfactant is typically present in an amount up to twice the weight, preferably up to the weight, of microcapsules. However, in the case of an aerosol the amount of surfactant is generally rather less than this. Surfactant can be incorporated in the walls of the microcapsules in an amount of up to 25% by weight of the microcapsules. Preferably, the amount is at least 1% by weight. Where more than 10% by weight is used, little useful additional effect is achieved. When microcapsules are exposed to surfactant to enable the surfactant to become coated on the microcapsule walls, typically the amount of surfactant to which the microcapsules are exposed is up to ten times, for example up to twice or more, the weight, preferably up to the weight, of the microcapsules.

Formulations according to the invention may be presented in a form suitable for inhalation. For this purpose, the formulations are generally loaded in an aerosol canister or, in dry powder form, in an inhaler. In an aerosol, the microcapsules are suspended in the propellant for the aerosol. In a dry powder inhaler, the microcapsules may be mixed with a diluent such as lactose. Typically, such microcapsules have had surfactant incorporated in their walls during the encapsulation procedure. In both ways, a fine suspension of microcapsules may be taken into the lungs by a patient. Typically, the aerosol canister or inhaler allows a metered dose of a drug such as a bronchodilating agent to be inhaled. This is generally achieved by the provision of a valve which meters the amount of formulation, fluid in the case of an aerosol, discharged with each actuation.

The microcapsules may be contacted with the surfactant prior to loading in an aerosol. Preferably, however, the surfactant is provided with the microcapsules and the propellant for the aerosol in the aerosol cannister. In such an instance, the surfactant may be provided in an amount ranging down to 10% of the weight of the microcapsules. The concentration of surfactant in the mixture in the aerosol cannister is typically no more than 5% by weight, preferably from 0.01 to 1% by weight. In the case of microcapsules for a dry powder inhaler, the surfactant is incorporated in the microcapsule walls prior to loading the inhaler with the microcapsules.

Formulations according to the invention may alternatively be ingested orally. The microcapsules are exposed to surfactant and suspended in a pharmaceutically acceptable water-immiscible oil. The oil is typically liquid, a fixed oil such as a fatty acid ester of glycerol. For example, the oil may be cotton seed oil or ethyl oleate. This suspension is then emulsified in an aqueous medium. By altering the drug loading in the microcapsules and by varying the relative concentrations of surfactants and oil, it is possible to alter the amount of drug immediately available in the aqueous phase of the mixture as well as control the rate of release of drug from the mixture into systems which mimic oral absorption.

The formulations are administered to a patient by inhalation or orally. A therapeutically effective amount is taken by a patient. Dosages depend upon the condition being treated, the stage the condition has reached, the patient under treatment and the drug being administered. Typically, however, one or two doses per day of a formulation of the invention may be given to a patient.

In a preferred embodiment where a bronchodilating agent is encapsulated for inhalation, asthma, bronchitis and other diseases of the respiratory system may be treated. The amount of formulation administered depends on the particular disease or disorder being treated and the type of bronchodilating agent being administered. Generally, however, the formulations may be inhaled only once or twice during a day. Thus, a formulation may be inhaled on two occasions per day, with an eight to twelve hour gap before the second inhalation, in an amount sufficient to deliver from 50 ug to 2 mg, more preferably 100 to 500 ug, of bronchodilating agent to the lungs per occasion. The dosage for salbutamol, for example, may be two inhalations of 100 ug each. This contrasts with the recommended dose for conventional salbutamol aerosol inhalations of 1 to 2 inhalations, each of 100 ug, every three to four hours up to a maximum of eight per twenty hours (Martindale, The Extra Pharmacopoeia, 28th edition, 1982). The dosage for terbutaline may be two inhalations each of 250 ug.

The following Examples 1 to 6 illustrate the invention.

Figure 2:
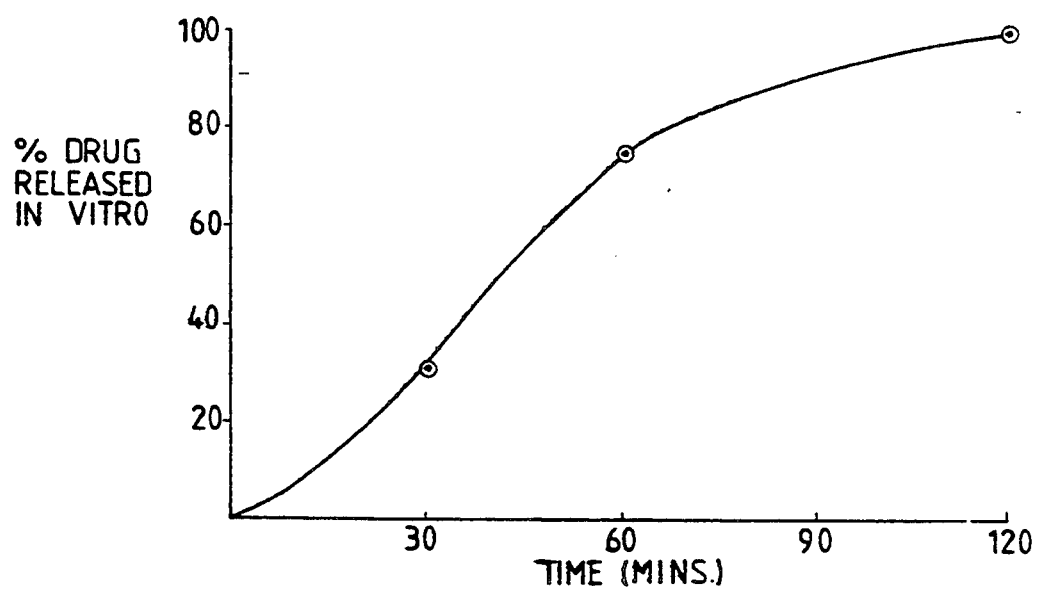

A BRIEF DESCRIPTION OF THE DRAWINGS:

FIG. 1 shows the results of the assays of the supernatant for terbutaline sulphate in Example 2; and FIG. 2 shows the results of the dissolution test in Example 2.

Reference Example

Preparation of terbutaline microcapsules

Terbutaline sulphate microcapsules were prepared using a Buchi 190 Mini spray-dryer equipped with a 0.7-mm spray nozzle (Brinkmann Instruments Co, Westbury, N.Y.). The spray-drying procedure was conducted as follows:

A 1.25 wt % polylactide-glycolide copolymer (DL-PLG) solution was prepared using methylene chloride as the solvent. After complete dissolution of the polymer, terbutaline sulphate was added to the polymer solution in an amount equalling the weight of DL-PLG. The terbutaline sulphate particles were then suspended by homogenization using a Brinkmann Polytron homogenizer (Brinkmann Instruments Co, Westbury N.Y.). Immediately after the homogenization was completed, the drug/polymer mixture was pumped into the nozzle of the spray dryer at a flow rate of approximately 1 ml/min. To effect aerosolization, nitrogen was also directed through the nozzle. The nitrogen pressure was maintained at about 103 KPa (15 lbs/in$^2$). The temperature of the spray-dryer chamber was kept at approximately 70° C. After all of the drug/polymer mixture was processed, the spray dryer was allowed to gradually cool to room temperature and the microcapsule product was collected.

Example 1

Effect of sorbitan trioleate on the in vitro release of terbutaline from microcapsules Solutions of sorbitan trioleate (Span 85) were prepared as follows. Into a 113 g (4 oz) glass jar, 150 to 160 g of Freon was added via a gas cylinder. Next, an appropriate amount of Span 85 was added to each jar. To prepare 1% Span 85 in Freon, approximately 1.5 g of Span 85 was weighed into a weigh boat and poured into the jar containing the Freon. To prepare more dilute surfactant solutions it was necessary to add the Span 85 surfactant via a pipette. It was determined that 10 drops of Span 85 weighed approximately 150 mg. Therefore 1 drop weighs approximately 15 mg.

| Solutions prepared | Span 85 added | Freon wt |
| --- | --- | --- |
| 1% span 85 | ~1.5 g | 156.4 g |
| 0.25% | 25 drops | 158.0 g |
| 0.10% | 10 drops | 161.2 g |
| 0.01% | 1 drop | 150.7 g |

After the surfactant was added, the jars were capped with Teflon-lined screw caps and shaken. The jars were stored at −70° C.

Microcapsules were weighed into plastic scintillation vials and different surfactant solutions were added to each vial individually. The vials were labelled accordingly, and a stir bar was added to each vial. The sample was allowed to stir uncovered for approximately 4 hours at room temperature. The samples were then placed under a hood and exposed to continuous air flow for 30 min to remove all traces of the Freon. The microcapsule/Span 85 mixture was then scraped from the vial.

An amount of microcapsules which contained approximately 15 mg of terbutaline sulphate was weighed out in triplicate and placed into small nylon pouches. These pouches consisted of 5 um, nylon mesh (Small Parts Inc., Miami, Fla.), and were 3.81 cm×3.81 cm (1.5 in×1.5 in). The pouches were formed by heat sealing the edges with a hot spatula blade. The microcapsules were sealed within the pouch by this method as well.

A nylon pouch containing the microcapsules was then placed in a 227 g (8 oz) glass jar, and 200 ml of deionized water was then added. Next, the glass jar was placed in a shakerbath maintained at 37° C. and oscillating at a rate of about 120 cycles/min. Aliquots were then removed periodically from the receiving fluid and assayed spectrophotometrically at 227 nm to determine their terbutaline sulphate concentrations. The amounts of terbutaline sulphate released was then calculated by using the highest recorded absorbance to determine 100% release of drug from the microcapsules. After the maximum or 100% release was obtained, the % release was determined proportionally. To illustrate, the following data were obtained for Microcapsule Batch D743-021 after exposure to 0.10% Span 85 in Freon.

| Time    | Abs. = 227 nm | Conc (ug/ml) | % Released |
|---------|---------------|--------------|------------|
| 5 min   | 1.443         | 74.0         | 83.5       |
| 15 min  | 1.650         | 85.4         | 96.4       |
| 30 min  | 1.693         | 87.6         | 98.9       |
| 1 h     | 1.711         | 88.6         | 100.0      |

Thus the maximum absorbance as determined spectrophotometrically at 227 nm was 88.6 ug/mL. This was determined via a standard curve which was done previously. After determining the maximum release at 1 h of 88.6 ug/mL, the percent release at the earlier times was calculated proportionally. For example, the release at 5 min was calculated as follows:

$$\frac{74.0 \text{ ug/mL}}{88.6 \text{ ug/mL}} \times 100\% = 83.5\%$$

The results are shown in Table 1 below.

Example 2

Liquid oral terbutaline formulation

Microcapsules of terbutaline sulphate were produced by spray drying according to the Reference Example. The particle sizes of the microcapsules were from 1 to 10 um. The microcapsules were mixed with sorbitan trioleate surfactant; then mixed with the oil, ethyl oleate; and finally emulsified in water by first adding the non-ionic surfactant Cremophor EL to the oil and microcapsule mixture and then adding quantities of water with vigorous mixing. The weight ratio of terbutaline microcapsules: sorbitan trioleate was about 1:5. The following quantitative formula was employed:

| Terbutaline microcapsules | 174 mg |
|---------------------------|--------|
| Sorbitan trioleate        | 1 ml   |
| ethyl oleate              | 5 ml   |
| Cremophor EL              | 5 ml   |
| Water QS                  | 100 ml |

The aqueous supernatant was assayed for terbutaline content on the 1st, 5th and 14th day after production. Furthermore after the 14th day a 20 ml sample of this mixture was exposed to the standard USP dissolution test run in pH 6.8 buffer at 37° C. and a stirring frequency of 50 cycles/min. The results are shown in FIGS. 1 and 2.

In FIG. 1, the data from the assays of supernatant when the mixture was stored for 14 days are presented. It is clear from this Figure that the concentration of terbutaline sulphate in the aqueous phase on the 1st day after production was 8.9% of the total terbutaline concentration and at 14 days the concentration was the same. By contrast the results in FIG. 2 present data for the in vitro dissolution of this same liquid formulation. This pharmacopoeia test is the same as that recommended for many tablet and capsule long acting formulations. In FIG. 2 it is quite apparent that when the mixture was exposed to this USP test, drug dissolved slowly but completely in the aqueous media over a 2 hour period.

Example 3

Preparation of Aerosols containing Microcapsules

Experimental aerosols were prepared by adding an appropriate quantity of microcapsules of terbutaline sulphate to an empty aluminium canister. The microcapsules were produced by spray-drying according to the Reference Example. They were designated batch D743-055-1. Their core loading of terbutaline sulphate was 26.6% by weight. The amount of terbutaline sulphate released from the microcapsules, in the absence of surfactant, was measured in vitro by the procedure described in Example 1. The percentages by weight of terbutaline sulphate released after 5, 10 and 30 mins were 84.5%, 98.6% and 98.8%, respectively.

The remaining ingredients for the aerosol, suitably cooled, were added. A metered valve capable of delivering 25 ul of the mixture was crimped to the canister to provide a seal. The following aerosols were prepared:

| Aerosol No. 1 | |
|---|---|
| Microcapsule batch D743-055-1 | 200 mg |
| Sorbitan Trioleate | 140 mg |
| Trichlorofluoromethane (Propellant 11 BP 80) | 3.44 g |
| Dichlorotetrafluoroethane (Propellant 114 BP 80) | 3.44 g |
| Dichlorodifluoromethane (Propellant 12 BP 80) | 6.88 g |
| Aerosol No. 2 | |
| Microcapsule batch D743-055-1 | 200 mg |
| Trichlorofluoromethane (Propellant 11 BP 80) | 3.44 g |
| Dichlorotetrafluoroethane (Propellant 114 BP 80) | 3.44 g |
| Dichlorodifluoromethane (Propellant 12 BP 80) | 6.88 g |

Example 4

In vivo studies involving terbutaline microcapsules

Aerosols prepared as described in Example 3 were tested in human volunteers. In one experiment, Aerosol No. 1 was employed. The physiological effects produced by this aerosol were compared to similar effects produced in the volunteer by a commercially available terbutaline aerosol. The human volunteer inhaled 4 puffs from the commercially available terbutaline inhaler (total inhaled dose approximately 1 mg terbutaline sulphate) and, on another occasion, inhaled 8 puffs from Aerosol No. 1 (inhaled dose approximately 1 mg terbutaline sulphate). Airway resistance was measured at regular intervals following inhalation of the drug substance, utilising a constant volume body plethysmograph and expressed as specific airway conductance (sGaw). This method has been described by others, for instance see J E Harvey and A E Tattersfield Thorax 1982; 37: 280–287. The results of this experiment are given in Table 2 below. Time here and in Table 3 is in minutes.

TABLE 2

| | % Change in sGaw | |
|---|---|---|
| Time | Commercial Aerosol | Aerosol No. 1 |
| 30 | 40 | 10 |
| 60 | 63 | 22 |

TABLE 2-continued

| | % Change in sGaw | |
|---|---|---|
| Time | Commercial Aerosol | Aerosol No. 1 |
| 120 | 36 | 22 |
| 240 | 40 | 22 |
| 360 | 10 | 20 |
| 420 | 0 | 22 |

A second experiment was carried out using another human volunteer. Aerosol No. 2 of Example 3 was compared against a standard terbutaline aerosol. In this case the volunteer inhaled 4 puffs of the experimental formulation and 2 puffs from the standard inhaler, SGaw was again measured at regular intervals as described above. The results from this experiment are given in Table 3 below.

TABLE 3

| | % Change in sGAw | |
|---|---|---|
| Time | Commercial Aerosol | Aerosol No. 2 |
| 30 | 47 | 10 |
| 60 | 47 | 30 |
| 120 | 22 | 39 |
| 240 | 6 | 13 |

The data presented in Tables 2 and 3 clearly indicates that Aerosols Nos. 1 and 2, containing microencapsulated terbutaline, were capable of prolonging the effect of the drug on sGaw. Comparing the results from the first and second experiments indicates that the sorbitan trioleate component of the aerosol mixture also had a significant influence on the results. It is clear that the initial response to terbutaline from Aerosol No. 1 was substantially depressed and that the response was constant for up to six hours. By comparison, the maximum pharmacological effect for Aerosol No 2 was delayed by approximately one hour as a result of the microencapsulation of the drug. The response was not constant and was in steep decline by the time of four hours. These data clearly indicate that the surfactant prolongs the effect of the inhaled microcapsule formulation.

Example 5

Preparation of Microcapsules incorporating Surfactant in their wall material Salbutamol suphate microcapsules containing Span 85 were prepared using a Buchi 190 Mini spray-dryer equipped with a 0.7 mm spray nozzle (Brinkmann Instruments Co, Westbury, N.Y.). The spray-drying procedure was conducted as follows.

A DL-PLG solution (0.80 wt %) was prepared using methylene chloride as the solvent. After complete dissolution of the polymer the Span 85 was added. An amount of Span 85 was added such as to obtain a core loading of surfactant of 10% by weight. After the Span 85 was dispersed throughout the solution, the salbutamol sulphate was added. An amount of salbutamol sulphate was added such as to obtain a core loading of drug desired of 20.1% by weight. The salbutamol sulphate particles were then suspended by homogenisation using a Brinkmann Polytron homogeniser (Brinkmann Instruments Co, Westbury, N.Y.). To perform this homogenisation procedure, the probe of the homogeniser was submerged in the polymer/drug mixture. The homogeniser was operated at a setting of approximately 6. The mixture was homogenised for three 30 second bursts, allowing 30 seconds between each burst.

Immediately after the homogenisation procedure, the polymer/drug mixture was placed on a stir plate and stirred vigorously to ensure that the salbutamol sulphate particles remained in suspension. A Gilson Minipulse 2 pump (Gilson Medical Electronics Inc, Middleton, Wis.) was then used to pump the mixture into the nozzle of the spray-dryer. A flow rate of approximately 1 ml/min was attained using size-14 Viton tubing (Cole-Parmer Instrument and Equipment Co, Chicago, Ill.). A small piece of aluminium foil was wrapped securely around the tubing and the mouth of the solvent jar to prevent loss of methylene chloride through evaporation.

To effect aerosolisation, nitrogen was directed through the nozzle of the spray-dryer. The nitrogen pressure was maintained at about 103 KPa (15 $lb/in^2$), as determined by the regulator on the nitrogen tank. The temperature of the spray-dryer's inlet chamber was maintained at about 50° C., while the collection chamber was kept at approximately 40° C. After all of the mixture was processed, the spray-dryer was allowed to gradually cool to room temperature and the microcapsule product was collected.

Example 6

Measurement of In Vitro Release Rate from Microcapsules incorporating Surfactant in their wall material In order to simulate release of drug in the lungs, a simple dissolution/diffusion apparatus was utilised. In this system, accurately weighed amounts of salbutamol-containing microcapsules prepared according to Example 5, of salbutamol-containing microcapsules prepared according to Example 5 but without Span 85 or pure salbutamol were placed inside a sealed piece of dialysis tubing. The pieces of tubing were then suspended in beakers containing 150 ml of pH 7.4 buffer. The buffer was stirred at a constant rate. Small samples were taken from the fluid in the beakers at regular intervals and assayed for active drug using the following procedure:

Samples of the buffer were injected directly on an HPLC fitted with a 2-Module with Novopak column and Guardpak pre-column, and a fluorescence detector set at 230 nm excitation with no emission filter. The solvent employed was a 4:96 acetonitrile/water with TEA adjusted to pH3 with orthophosphroic acid, and the flow rate was 2.5 ml per minute.

The release of salbutamol from the two different batches of microcapsules, one with and the other without surfactant, is demonstrated in Table 4 below. Clearly, the presence of the Span surfactant within the microcapsulses substantially delayed the release of the drug.

Example 7

Salbutamol microcapsules were prepared using the reference method and an in vitro release study was carried out as described in Example 1 except that oleic acid was used as the surfactant instead of sorbitan trioleate. The results obtained are shown in Table 5 below.

TABLE 1

RESULTS OF SURFACTANT INTERACTION EXPERIMENTS

| Microcapsule Batch | Core Loading, wt % terbutaline sulfate | Microcapsule: Span 85 wt ratio | in Vitro release kinetics, % terbutaline sulfate released at | | | | | |
|---|---|---|---|---|---|---|---|---|
| | | | 5 min | 15 min | 30 min | 1 h | 3 h | 24 h |
| D743-021 | 51.6 | 1:0 | 57.2 | 92.4 | 99.8 | 100 | ND[a] | ND |
| D743-021 | 51.6 | 1:1.5 | 83.5 | 96.4 | 98.9 | 100 | ND | ND |
| D743-021 | 51.6 | 1:3.75 | 4.7 | 17.7 | 30.7 | 50.9 | 68.8 | 100 |
| D743-021 | 51.6 | 1:15 | 0.0 | 1.9 | 8.4 | 14.6 | 26.7 | 100 |
| D743-029 | 60.3 | 1:3 | 91.8 | 95.6 | 97.4 | 99.8 | 100 | ND |
| D743-029 | 60.3 | 1:7.5 | 18.9 | 33.1 | 50.5 | 64.1 | 84.0 | 100 |
| D743-051 | 10.8 | 1:0 | 81.7 | 94.0 | 98.7 | 100 | ND | ND |
| D743-051 | 10.8 | 1:1.5 | 45.3 | 58.2 | 64.5 | 73.5 | 83.5 | 100 |
| D743-051 | 10.8 | 1:3.75 | 1.3 | 15.1 | 19.1 | 25.3 | 35.3 | 85.2 |

[a]ND = Not determined.

TABLE 4

IN VITRO RELEASE OF SALBUTAMOL FROM MICROCAPSULES

| BATCH | LOADING | SURFACTANT(%)* | TIME (HRS) | | | | | | | |
|---|---|---|---|---|---|---|---|---|---|---|
| | | | .25 | .5 | .75 | 1 | 2 | 3 | 4 | 6 |
| E122-007-1 | 23.2 | 0 | 16.5 | 31.5 | 50.5 | 60.4 | 89.7 | 100 | | |
| E122-119-1 | 20.1 | 10 | 6.5 | 10.7 | 14.8 | 16.8 | 42.6 | 73.5 | 85.9 | 98.3 |

*sorbitan trioleate

TABLE 5

IN VITRO RELEASE KINETICS OF MICROCAPSULES CONTAINING 28.2 WT % SALBUTAMOL SULFATE AFTER EXPOSURE TO OLEIC ACID/FREON MIXTURES

| Ratio of microcapsules to oleic acid | In vitro release kinaties, | | | | % of core material release at | | | | |
|---|---|---|---|---|---|---|---|---|---|
| | 5 min | 15 min | 30 min | 1 h | 2 h | 4 h | 6 h | 24 h | 48 h |
| 1:1 | 5.3 | 17.3 | 27.2 | 32.6 | 45.2 | 53.7 | 58.0 | 90.4 | 100.0 |
| 5:1 | 50.5 | 84.5 | 93.1 | 96.5 | ND | ND | ND | 100.0 | |
| 10:1 | 55.7 | 90.7 | 97.4 | ND | 99.2 | ND | ND | 99.6 | 100.0 |
| 25:1 | 71.0 | 97.7 | 97.7 | 98.5 | 99.6 | ND | ND | 100.0 | |

ND = Not Determined

We claim:

1. A pharmaceutical formulation suitable for inhalation, comprising:
   (i) microcapsules having an average diameter of from 0.1 to 10 μm which consist essentially of a biodegradable, biocompatible wall-forming polymer encapsulating a drug, the polymer having a molecular weight of greater than 10,000 daltons, and
   (ii) a lipid-soluble surfactant which is selected from the group consisting of sorbitan trioleate, sorbitan monolaurate, sorbitan monooleate, sorbitan monopalmitate, sorbitan monostearate, a polyoxamer and a surface active fatty acid, which is present in an amount of from 1 to 25% by weight of the microcapsules and which is incorporated within the polymer forming the wall of the microcapsules.

2. A pharmaceutical formulation suitable for ingestion, comprising:
   (i) microcapsules having an average diameter of from 0.1 to 20 μm which consist essentially of a biodegradable, biocompatible wall-forming polymer encapsulating a drug, the polymer having a molecular weight of greater than 10,000 daltons, and
   (ii) a lipid-soluble surfactant which is selected from the group consisting of sorbitan trioleate, sorbitan monolaurate, sorbitan monooleate, sorbitan monopalmitate, sorbitan monostearate, a polyoxamer and a surface active fatty acid, which is present in an amount of from 1 to 25% by weight of the microcapsules and which is incorporated within the polymer forming the wall of the microcapsules.

3. A process for the preparation of a pharmaceutical formulation which is suitable for inhalation and which comprises:
   (i) microcapsules having an average diameter of from 0.1 to 10 μm which consist essentially of a biodegradable, biocompatible wall-forming polymer encapsulating a drug, and
   (ii) a lipid-soluble surfactant which is selected from the group consisting of sorbitan trioleate, sorbitan monolaurate, sorbitan monooleate, sorbitan monopalmitate, sorbitan monostearate, a polyoxamer and a surface active fatty acid, which is present in an amount of from 1 to 25% by weight of the microcapsules and which is incorporated within the polymer forming the wall of the microcapsules,
   the process comprising
   (a) forming a solution comprising a solvent, a biodegradable, biocompatible wall-forming polymer and a lipid soluble surfactant,
   (b) adding a drug to the solution thus formed, and
   (c) evaporating off the solvent to obtain microcapsules having an average diameter of from 0.1 to 10 μm.

4. A process for the preparation of a pharmaceutical formulation which is suitable for ingestion and which comprises:
   (i) microcapsules having an average diameter of from 0.1 to 20 μm which consist essentially of a biodegradable, biocompatible wall-forming polymer encapsulating a drug, and
   (ii) a lipid-soluble surfactant which is selected from the group consisting of sorbitan trioleate, sorbitan monolaurate, sorbitan monooleate, sorbitan monopalmitate, sorbitan monostearate, a polyoxamer and a surface active fatty acid, which is present in an amount of from 1 to 25% by weight of the microcapsules and which is incorporated within the polymer forming the wall of the microcapsules, the process comprising (a) forming a solution comprising a solvent, a biodegradable, biocompatible wall-forming polymer and a lipid soluble surfactant, (b) adding a drug to the solution thus formed, and (c) evaporating off the solvent to obtain microcapsules having an average diameter of from 0.1 to 20 μm.

5. A formulation according to claim 1, which is in the form of an aerosol for inhalation.

6. A formulation according to claim 1, which is in the form of a dry powder for inhalation and wherein from 1 to 10% by weight of surfactant is incorporated in the walls of the microcapsules.

7. A formulation according to claim 1 wherein the drug is selected from the group consisting of an antibiotic, cardiovascular drug, an anti-convulsant and chemotherapeutic agents for cancer treatment.

8. A formulation according to claim 1, wherein the drug is a bronchodilating agent or other anti-asthma drug selected from the group consisting of corticosteroids, disodium cromoglycate and antihistamines.

9. A formulation according to claim 8, wherein the bronchodilating agent is a beta-adrenergic agonist, a xanthine, an anti-cholinergic agent, a calcium antagonist or a leukotriene.

10. A formulation according to claim 9, wherein the drug is salbutamol or terbutaline.

11. A formulation according to claim 2, wherein the drug is selected from the group consisting of an antibiotic, cardiovascular drug, an anti-convulsant and chemotherapeutic agents for cancer treatment.

12. A formulation according to claim 6, wherein the drugs is a bronchodilating agent or other anti-asthma drug selected from the group consisting of corticosteroids, disodium cromoglycate and antihistamines.

13. A formulation according to claim 12, wherein the bronchodilating agent is a beta-adrenergic agonist, a xanthine, an anti-cholinergic agent, a calcium antagonist or a leukotriene.

14. A formulation according to claim 13, wherein the drug is salbutamol or terbutaline.

15. A process according to claim 3, wherein the solvent evaporation in step (c) is effected by passing the solution through a spray drier nozzle together with an inert gas so as to form an aerosol of microcapsules, and collecting the microcapsules.

16. A process according to claim 4, wherein the solvent evaporation in step (c) is effected by passing the solution through a spray drier nozzle together with an inert gas so as to form an aerosol of microcapsules, and collecting the microcapsules.

17. A pharmaceutical formulation suitable for inhalation, comprising (i) microcapsules having an average diameter of from 0.1 to 10 μm which consist essentially of a biodegradable, biocompatible wall-forming polymer encapsulating a drug, the polymer having a molecular weight of greater than 10,000 daltons, and (ii) a lipid soluble surfactant which is a sorbitan fatty acid ester, which is present in an amount from 1 to 25% by weight of the microcapsules and which is incorporated within the polymer forming the wall of the microcapsules.

18. A pharmaceutical formulation according to claim 7, wherein the lipid soluble surfactant is sorbitan trioleate.

19. A formulation according to claim 17, which is in the form of an aerosol for inhalation.

20. A formulation according to claim 17, which is in the form of a dry powder for inhalation and wherein from 1 to 10% by weight of surfactant is incorporated in the walls of the microcapsules.

21. A formulation according to claim 17, wherein the drug is selected from the group consisting of an antibiotic, a cardiovascular drug, an anti-convulsant and chemotherapeutic agents for cancer treatment.

22. A formulation according to claim 17, wherein the drug is a bronchodilating agent or other anti-asthma drug selected from corticosteroids, disodium cromoglycate and antihistamines.

23. A pharmaceutical formulation suitable for ingestion, comprising (i) microcapsules having an average diameter of from 0.1 to 20 μm which consist essentially of a biodegradable, biocompatible wall-forming polymer encapsulating a drug, the polymer having a molecular weight of greater than 10,000 daltons, and (ii) a lipid soluble surfactant which is a sorbitan fatty acid ester, which is present in an amount of from 1 to 25% by weight of the microcapsules and which is incorporated within the polymer forming the wall of the microcapsules.

24. A pharmaceutical formulation according to claim 23, wherein the lipid soluble surfactant is sorbitan trioleate.

25. A formulation according to claim 23, wherein the drug is selected from the group consisting of an antibiotic, a cardiovascular drug, an anti-convulsant and chemotherapeutic agents for cancer treatment.

* * * * *

UNITED STATES PATENT AND TRADEMARK OFFICE
CERTIFICATE OF CORRECTION

PATENT NO. : 5,384,133
DATED : January 24, 1995
INVENTOR(S) : Boyes, et al

It is certified that error appears in the above-indentified patent and that said Letters Patent is hereby corrected as shown below:

On the Title Page Under Related U.S Application Data, "PCT/6B87/00566" should be --PCT/GB87/00566--.

On the Title Page under U.S. Patent Documents, reference 4,952,402, "Sparks" should be --Sparks, et al--.

Column 6, line 36, "~1.5 g" should be --¯1.5 g--.

Column 6, line 58, "cmx3.81" should be --cm x 3.81--.

Column 7, line 11, "(ug/ml)" should be --(ug/mL)--.

Columns 11,12, Table I, line 11, "64.1" should be --64.7--.

Column 14, line 19, Claim 18, "7" should be --17--.

Signed and Sealed this

Twenty-fifth Day of April, 1995

Attest:

BRUCE LEHMAN

*Attesting Officer*          *Commissioner of Patents and Trademarks*